(12) United States Patent
Jensen et al.

(10) Patent No.: US 11,051,735 B2
(45) Date of Patent: Jul. 6, 2021

(54) PRESSURE MONITORING SYSTEM

(71) Applicant: Medical Measurement Systems B.V., Enschede (NL)

(72) Inventors: Michael Gondy Jensen, Jyderup (DK); Jens Witte, Munich (DE); David Van Gorkom, Prien am Chiemsee (DE); Kristine Larsen, Munich (DE)

(73) Assignee: MEDICAL MEASUREMENT SYSTEMS B.V., Enschede (NL)

( * ) Notice: Subject to any disclaimer, the term of this patent is extended or adjusted under 35 U.S.C. 154(b) by 0 days.

(21) Appl. No.: 16/785,619

(22) Filed: Feb. 9, 2020

(65) Prior Publication Data
US 2020/0315513 A1 Oct. 8, 2020

Related U.S. Application Data

(63) Continuation of application No. 14/772,350, filed as application No. PCT/EP2018/070878 on Aug. 1, 2018, now Pat. No. 10,595,765.

(30) Foreign Application Priority Data

Aug. 1, 2017 (DE) .......................... 102017117436.2

(51) Int. Cl.
*A61B 5/20* (2006.01)
*A61B 5/00* (2006.01)
(Continued)

(52) U.S. Cl.
CPC ................ *A61B 5/205* (2013.01); *A61B 5/42* (2013.01); *A61M 39/10* (2013.01); *A61M 39/28* (2013.01); *B30B 15/161* (2013.01); *B30B 15/163* (2013.01); *B30B 15/186* (2013.01); *F15B 7/006* (2013.01); *F15B 11/022* (2013.01); *A61B 2560/0223* (2013.01); *A61M 5/14232* (2013.01); *A61M 5/168* (2013.01); *A61M 2025/0003* (2013.01); *A61M 2205/3344* (2013.01); *A61M 2205/3348* (2013.01); *F15B 2211/20515* (2013.01); *F15B 2211/20546* (2013.01); *F15B 2211/27* (2013.01); *F15B 2211/6651* (2013.01); *F15B 2211/7107* (2013.01); *F15B 2211/775* (2013.01)

(58) Field of Classification Search
None
See application file for complete search history.

(56) References Cited

U.S. PATENT DOCUMENTS 4,621,647 A * 11/1986 Loveland ............ A61M 27/006
600/487
4,858,619 A * 8/1989 Toth ...................... A61B 5/031
600/561

(Continued)

*Primary Examiner* — Patrick Fernandes
*Assistant Examiner* — Benjamin S Melhus
(74) *Attorney, Agent, or Firm* — Douglas Denninger

(57) ABSTRACT

A pressure-measuring system, including a tube system having at least first and second pressure measuring devices, each including a pressure transducer membrane and a measuring chamber. A first flow regulation device with a perfusion tube section is positioned between the first pressure measuring device and a supply of fluid, and has a first tube clamp that acts on a tube section by squeezing. The system further includes at least one non-perfusion regulation device.

18 Claims, 6 Drawing Sheets

(51) Int. Cl.
*A61M 39/10* (2006.01)
*A61M 39/28* (2006.01)
*B30B 15/16* (2006.01)
*B30B 15/18* (2006.01)
*F15B 7/00* (2006.01)
*F15B 11/02* (2006.01)
*A61M 5/168* (2006.01)
*A61M 5/142* (2006.01)
*A61M 25/00* (2006.01)

(56) References Cited

U.S. PATENT DOCUMENTS

| | | | | |
|---|---|---|---|---|
| 4,949,723 | A * | 8/1990 | Wallace | A61B 5/021 600/485 |
| 4,960,127 | A * | 10/1990 | Noce | A61B 5/0215 600/488 |
| 5,097,840 | A * | 3/1992 | Wallace | A61B 5/021 137/625.17 |
| 5,207,641 | A * | 5/1993 | Allton | A61M 16/0463 137/625.22 |
| 5,318,546 | A * | 6/1994 | Bierman | A61M 39/284 128/898 |
| 5,581,038 | A * | 12/1996 | Lampropoulos | A61B 5/0215 73/721 |
| 2003/0181850 | A1* | 9/2003 | Diamond | A61M 39/223 604/30 |
| 2014/0107527 | A1* | 4/2014 | Dijkman | A61B 5/205 600/561 |
| 2021/0000361 | A1* | 1/2021 | Lark | A61B 5/205 |

* cited by examiner

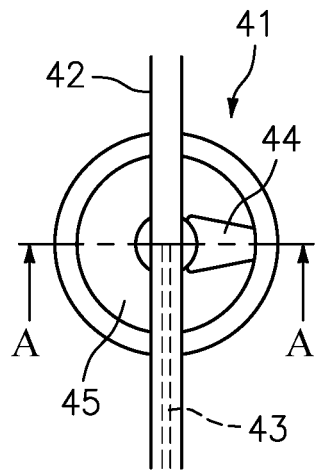
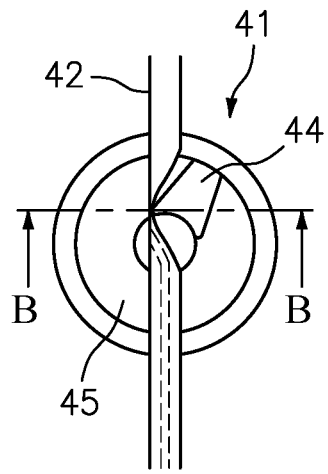
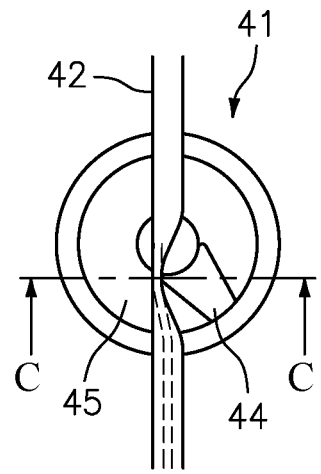
FIG. 3a          FIG. 3b          FIG. 3c
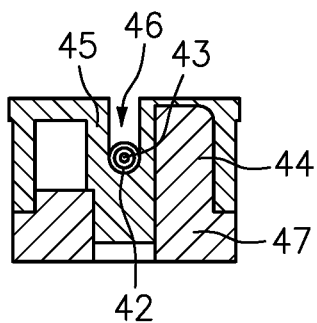
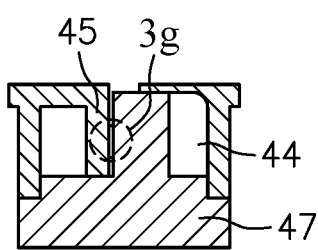
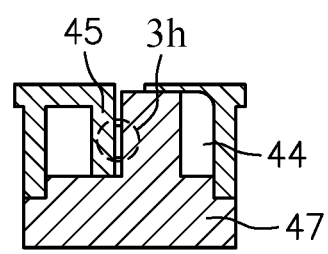
FIG. 3d          FIG. 3e          FIG. 3f
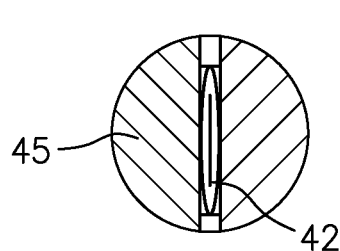
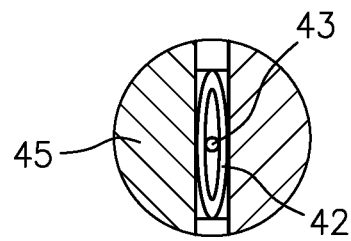
FIG. 3g          FIG. 3h

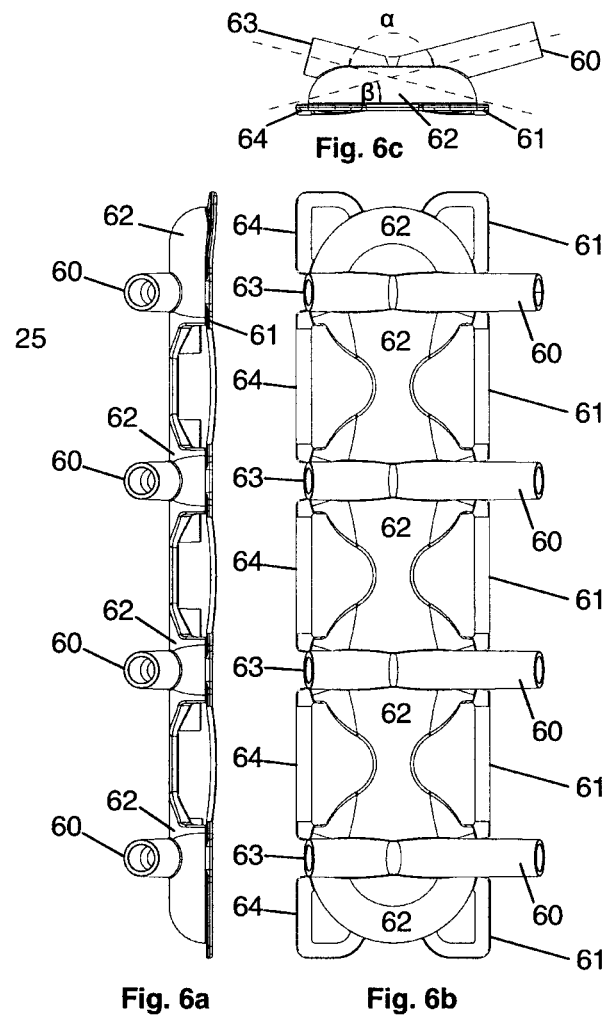
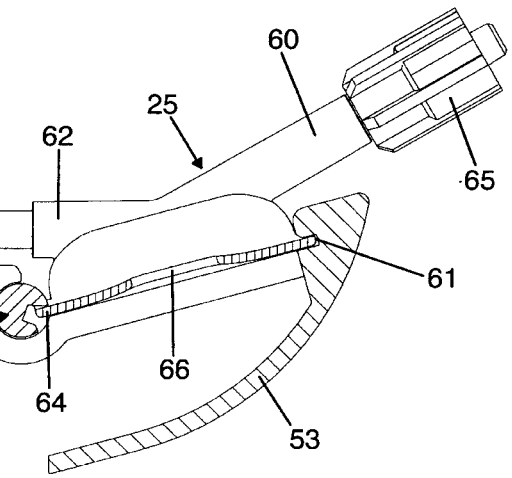

PRESSURE MONITORING SYSTEM

CROSS-REFERENCE TO RELATED APPLICATIONS

This application is a continuation of U.S. application Ser. No. 14/772,350, now U.S. Pat. No. 10,595,765, which was a national phase filing on Sep. 2, 2015 under 35 USC § 371 of international application No. PCT/EP2014/053968 filed 28 Feb. 2014, which claims priority to German Application No. 10 2013 102 083.6 filed 4 Mar. 2013. This application also cross-references the following two US applications by the same inventors and having the same filing dates in the US, WIPO and Germany: Ser. No. 14/772,351 for "Device For Measuring Pressure In A Fluid" and Ser. No. 14/772,355 for "Device For Regulating A Volumetric Flow Rate". The entire contents of each of the above-mentioned applications are incorporated herein by reference.

FIELD OF THE INVENTION

The present invention relates to pressure-measuring system, more particularly for medical diagnosis, a method of venting and zeroing the pressure-measuring system and the use of the system in the field of urodynamics and gastroenterology.

BACKGROUND OF THE INVENTION

In the prior art, diagnostic pressure measurement in familiar, particular in urodynamics. Pressure measurement with water-filled disposable catheters is the most widely used method in urodynamics, and due to its measuring quality and robustness is recommended as the golden standard by the ICT (International Continence Society=worldwide umbrella association for urodynamics).

In pressure measurement with water-filled catheters the pressure in the body is directed via a water column, which passes through the lumen of the catheter and the pressure transmission tubes, to external pressure sensors. There, the pressure in the body, including a hydrostatic pressure resulting from the difference in height between the measurement indicator and measurement site, is measured. This pressure offset is compensated either through defined positioning of the sensors (at the pubic bone in urodynamics) or through electronic zeroing.

Today, a urodynamic examination requires a considerable amount of preparation and a large number of sterile disposable articles are required. A pump tube, a perfusion tube, three measurement indicators each with a three-way and a two-way valve, three pressure transmission hoses, a transurethral catheter with a filling and two measuring volume and a rectal catheter with a balloon, which all have to be assembled and prepared on site (FIG. 1).

The strengths of this method known in the prior art include the absolutely superior measuring quality through outstanding impulse response times, high zeroing stability, low temperature drift and low hysteresis. The system-related, automatic compensation of the pressure offset on displacement of the measuring volume in the bladder is also important. In addition, the change in hydrostatic pressure in the bladder can inherently be balanced out through the coupled height of the water column of the pressure transmission tubes to the pressure measurement indicators.

Disadvantageous, however, is the very complicated, error-prone and time-consuming handling involved. Each of the various individual steps has to be carried out in the presence of, in most cases, restless to nervous patients, which even in the case of experienced users often leads to errors and a large number of disposable articles are needed, which frequently leads to logistical problems.

SUMMARY OF THE INVENTION

On the basis of this prior art, it is now the aim of the present invention to provide a device for measuring pressure in a fluid with which the known drawbacks of the prior art are at least partially overcome or improved.

This is achieved through a pressure-measuring system in accordance with the invention according to claim 1, a method of automatically venting and zeroing a corresponding pressure-measuring system according to claim 20. Preferred forms of embodiment of the system and method are the subject matter of the relevant sub-claims. The invention also covers the use of pressure-measuring system in the field of urodynamics and gastroenterology, more particularly for bladder pressure measurement.

The present invention comprises a pressure-measuring system with at least one measuring lumen which can be filled with a fluid, at least one tube system for connecting a fluid reservoir to the at last one measuring lumen and an arrangement or device for conveying the fluid through the at least one tube system. The invention is characterised in that the tube system comprises at least one first device for measuring pressure in a/the fluid and this device consists of a coupling element, at least one pressure transducer and at least one measuring chamber which can be filled with fluid. The coupling element preferably mechanically connects the measuring chamber via a membrane with the measuring area of the pressure transducer, wherein the measuring chamber has at least two connection points for the fluid or the fluid flow. In addition, between the first device for measuring pressure and the supply of the fluid, the tube system has a second device for regulating a volumetric flow, which in addition to a tube section through which fluid can flow has at least one tube clamp. Furthermore, the second device is designed in such a way that it can be set to the regulation positions open, closed and perfused, wherein in the closed position the lumen of the tube section is completely closed and in the perfused position, through a spacer in the inside of the tube section, which extends at least to the area of the clamping point of the tube clamp, the lumen is partly, more particularly slightly open.

Considered as fluids in accordance with the present invention are flowable systems, more particularly liquids, which are, for example, used in medicine and medical technology. Examples of these can be infusion solutions such as sodium chloride solution, water, aqueous solutions, solutions for injection, solutions for infusion, nutritional solutions, electrolyte solutions, blood, plasma, gas, air, combinations thereof and suchlike.

In accordance with a further particularly preferred form of embodiment these fluids are stored in fluid reservoirs which, in turn, are also known in the prior art, in the form of infusion bottles or infusion bags for example.

Considered as the measuring lumen in accordance with the present invention is the entire space of a tube system which can be filled with fluid, which in accordance with a particularly preferred form of embodiment is understood as extending from the fluid reservoir to, for example, the opening section of an application system, e.g. a catheter. In contrast to the measuring lumen, a measuring chamber is understood as a container or spatial volume, which is arranged in the immediate vicinity of the pressure transducer, i.e. the device for determining the pressure, and in which preferably in addition to the flow conditions the volume restricted therein is determined.

Understood as a coupling element in accordance with the present invention is one or a plurality of sections of the pressure-measuring device, with which preferably the measuring chamber which can be filled with fluid and its measuring area defined by a membrane can be connected to the pressure transducer/pressure sensor in such a way that the pressure is determinable within the measuring chamber. Such coupling elements can be, for example, snap-on elements or detachable plug-type connections, such as bayonet or similar connections, but can also be mechanically stoppable connection systems.

In accordance with the present invention at least the second device for regulating the volumetric flow can be set to three regulation positions comprising the positions open, closed and perfused. In accordance with the present invention perfused means a setting in which under predetermined conditions the volumetric flow, which can be determined by the device for regulating the fluid flow, is restricted to between 0.1 ml per minute and 8 ml per minute, preferably between 0.5 ml per minute and 5 ml per minute. Such a setting is required when very small volumetric flows are needed to carry out the corresponding pressure measurement in a dynamic system. In accordance with the present invention such volumetric flows are considered as small as they can be seen as relatively small in comparison with the normal/maximum volumetric flow.

In accordance with a further, particularly preferred form of embodiment, the coupling element has a clamping edge, which preferably has at least one rotatably borne pressing roller that can be positively and/or non-positively connected to the coupling device and the measuring chamber also has two webs arranged opposite each other which engage in a clamping edge or the pressing roller. The pressing roller preferably has an essentially axially extending slit into which one of the webs of the measuring chamber can be inserted and through this positively and/or non-positively connected. In accordance with a further particularly preferred form of embodiment the pressing roller can be moved manually or by means of a motor, more particularly a multiphase motor or series motor and is held or stopped in a predetermined position either mechanically or by means of this motor. These positions are at least the open position, i.e. in which the web can be introduced into the measuring chamber, and the close position in which the web is locked in place.

In accordance with the present invention the second device for regulating the volumetric flow comprises at least one tube clamp which is preferably arranged a basic housing with an accommodating area for the corresponding tube section. The tube clamp preferably also has a clamping element which can interact with at least one, preferably a plurality of sections of the accommodating area in the basic housing as pressing points and that provide at least two regulation positions in which the lumen of the tube section is open, closed and/or perfused, i.e. slightly open.

In accordance with a particularly preferred form of embodiment of the present invention the pressure-measuring system is characterised in that the regulation positions are effected by at least one tube clamp, wherein the clamping element is arranged in a rotating manner and extends radially around the centre of rotation. In particular the section of the clamping element closest to the centre of rotation interacts with at least one pressing point of the housing accommodation of housing accommodation area.

In a further particularly preferred form of embodiment the tube clamp comprises a basic housing with an accommodating area for one tube section and a clamping element which can be moved between two or three regulation positions. In at least one regulating position the clamping element in interaction with sections of the accommodating area as pressing points acts on the tube section and its lumen. Preferably, in accordance with another form of embodiment of the invention, a spacer is arranged in lumen of the corresponding tube section in one regulating position.

In an alternative, but also particularly preferred form of embodiment the clamping element is moved by means of a motor, more particularly a multiphase motor or a servo motor, between the regulation positions and preferably held/locked in these accordingly. For the individual positions stopping mechanisms can be provided or the multiphase motor or servo motor provides stops at the relevant positions. Alternatively the clamping element can also be moved into the appropriate position and, if necessary, mechanically fixed manually.

In accordance with a further, particularly preferred form of embodiment of the present invention the tube section is made of a flexible material, more particularly a flexible plastic, and is squeezable in sections, Such tube sections or tubes are known in the prior art. Additionally, such a tube section has a lumen. i.e. a clear diameter which is preferably between 0.2 mm and 10 mm, preferably between 0.5 mm and 5 mm and more particularly around approx. 3 mm.

In addition, a spacer can be provided in at least one tube section as an integral component, wherein in accordance with a further particularly preferred form of embodiment of the present invention the lumen of the tube is irregularly reduced by the spacer and/or the spacer is formed by a thread-like or rod-like element that irregularly reduces the lumen of the tube. Such spacers can be integrated into the sheath of the tube or preferably be connected positively, non-positively or bonded to the tube section. Here, in accordance with a particularly preferred form of embodiment these spacers reduce the lumen of the corresponding tube section between 0.01% to 5%, preferably between 0.1% and 1%, and more particularly around 0.5%.

In accordance with the present invention, in the appropriate regulation setting of the device for regulating the volumetric flow of the tube section the purpose of the spacer is to keep the tube section open in a so-called "perfused" manner so that only small volumetric flows of the fluid can pass through.

In accordance with a further particularly preferred form of embodiment of the pressure system in accordance with the invention the connection points to the measuring chamber are arranged at an angle $\alpha$ with regard to each other of between 180° and 60°, preferably at an angle of between 180° and 120°, particularly preferably at an angle of between 144° and 115°, more particularly at an angle of approx. 150°. In addition, and corresponding to this angle $\alpha$ the connection points are arranged at an angle $\beta$ of between 0° and 60°, preferably of between 12° and 18°, preferably of less than 60° and more particularly of approximately 15° with regard to the base area of the measurement chamber.

In accordance with a further preferred form of embodiment the measuring chamber can be designed so that it has a circular base area, in which, in accordance with another particularly preferred from of embodiment in which the membrane, which is directly or indirectly coupled to the pressure transducer, is arranged. This base can also be open, wherein preferably the base area is covered by the aforementioned membrane and the measuring chamber is connected to this membrane in a fluid-tight manner. Such membranes are preferably made of a material selected from a group that includes silicone, latex, rubber, combinations thereof or suchlike.

In accordance with a further particularly preferred form of embodiment of the present invention the pressure transducer, which determines the pressure in the measuring chamber via the membrane, is a so-called electromechanical pressure transducer the measuring area of which is preferably covered by the aforementioned membrane in a form-fitted manner and/or the measuring range of the pressure transducer is arranged centrically in relation to the base area of the measurement chamber. In accordance with a further preferred form of embodiment of the present invention the measuring chamber has an interior space which is essentially dome-shaped and in accordance with a further particularly preferred form of embodiment is flattened in the central area.

In a further particularly preferred form of embodiment of the present invention at least the tube clamp and/or the coupling element and/or the measuring chamber are at least in sections made of a material selected from a group which preferably includes duroplastic or thermoplastic synthetic materials, and more particularly polyphenylene sulphide, polypropylene, poly-1-butene, polyvinyl chloride, polyvinylidene chloride, polymethyl methacrylate, polyacryl nitrile, polystyrene, polyacetal, polyvinyl alcohol, polyvinyl acetate, ionomers, fluoroplastic, polyethylene, polyamide, more particularly partially aromatic polyamide, polycarbonate, polyester, polyphenylene oxide, polysulphone, polyvinyl acetal, polyurethane and chlorinated polyether, cellulose nitrate, cellulose acetate, cellulose ether, phenol resin, urea resin, thiourea resin, melamine resin, alkyl resin, allyl resin, silicone, polyimide, polybenzimidazole, epoxy resin, casein plastic, cross-lined polyurethane, unsaturated polyester resin, acrylnitrile butadiene styrene, acrylester styrene acrylonitrile, metals such as stainless steel, aluminium, combinations thereof and suchlike.

In addition, the device for conveying the fluid in accordance with the present invention is preferably a peristalsis pump or a displacement pump and more particularly a tube pump or a roller pump. Corresponding infusion pumps can also be used. Alternatively to the use of an appropriate mechanical or hydraulic pump, the provision of a so-called gravity pump through the arrangement of the corresponding fluid reservoir is also within the context of the present invention.

In addition to the above-described device of the present invention, the aim of the invention is also achieved through a method for automatically venting and zeroing a pressure system after positioning at least one measuring lumen. The methods includes, in addition the step of measuring the high pressure on the pressure transducer when the tube systems and measuring lumen are filled with air, the filling of the tube system and the measuring lumen with a fluid from the fluid reservoir and subsequent correction of the hydraulic pressure exerted through the difference in height between the sensor/the measuring chamber and the measuring lumen/measuring site through alignment with the previously determined rest pressure. Such a method is by itself but also in combination with the previously described device the subject matter of the present invention. Additionally, in a further particularly preferred form of embodiment of the present invention the measured rest pressure can be transferred to a control device and from the measurements, i.e. a plurality of measurements, a mean rest pressure can be determined.

In accordance with a further particularly preferred form of embodiment the method covers the correction of the hydrostatic pressure exerted through the difference in height between the measuring chamber and the sensor by way of alignment with the mean rest pressure. According to a further particularly preferred form of embodiment of the present invention the quantity of fluid used for filling essentially corresponds with the volume of the tube system and the measuring lumen and/or the infusion volume.

In accordance with a further particularly preferred form of embodiment, with the method according to the invention the filling process is ended when a quantity of fluid corresponding to the volume of the tube system and the measuring volume and/or the infusion volume has been pumped/supplied from the fluid reservoir into the tube system and the measuring lumen. Here, in accordance with a further particularly preferred form of embodiment the quantity of fluid pumped into the tube system and the measuring lumen or infusion lumen can be determined by way of rotations of the roller wheel of the pump or via volume transducer. As a further particularly preferred step of the method in accordance with the invention, before filling the tube system and measuring lumen the tube clamp as a component part of the device for regulating the fluid flow is automatically brought into the open position and after filling returned to the close regulating position. The context of the present invention includes the individual process stages being repeated when several pressure systems are used and preferably the process stages are carried out fully automatically after starting the process. As set out above, using the described measuring system for implementing the method in accordance with invention comes under the scope of the present invention.

In addition to the device for measuring pressure, the invention also comprises the use of the pressure-measuring system as describe above in the field of urodynamics and gastroenterology, more particular for bladder, rectal and urethral pressure measurement.

The invention will be described below with the aid of a preferred form of embodiment, wherein it is pointed out that the invention is not restricted to the illustrated embodiment but also covers appropriate deviations in the sense of the present invention.

BRIEF DESCRIPTION OF THE DRAWINGS

FIGS. 3a-3h show detailed views of the device for regulating the volumetric flow

FIGS. 6a to 6d show detailed views of the dome cassette and its locking arrangement on the pressure measuring sensors;

DETAILED DESCRIPTION OF THE CURRENTLY PREFERRED EMBODIMENTS

Figure 1:
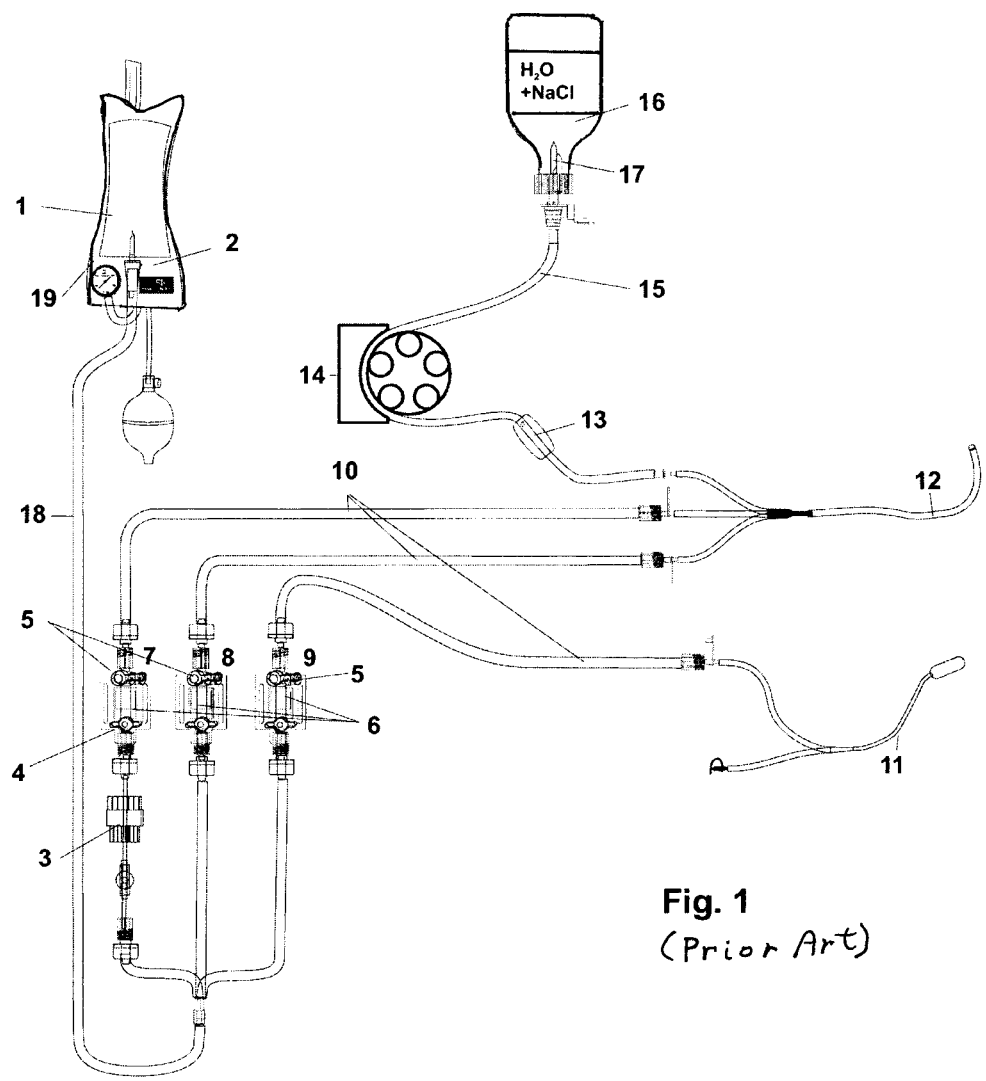
FIG. 1 shows the structure of a measuring system in accordance with the prior art.

FIG. 1 schematically shows the structure of a device for measuring pressure with water-filled disposable catheters. In addition to the bag with a solution for infusion 1 and a pressure cuff 2, a pressure transducer 3 and two-way valves 4 before the pressure sensors 6 are shown. Connected to these are three-way valves 5 and the corresponding tubes are designated as $P_{ura}$ 7, $P_{ves}$ and $P_{abd}$ 9. Via the pressure transmission hoses 10 the solution for infusion is supplied from the bag 1 to the rectal catheter 11 and the urethral pressure profile (UPP) catheter 12. In addition from the bottle 16 with, for example, a saline solution, via the roller pump 14 and the drip chamber 13, the saline solution is supplied to the UPP catheter 12 from the bottle 16.

The preparation and measuring procedure is carried out as follows:

a) The pump tube 15 is inserted into the pump 14 and the spike connection 12 of the tube inserted into the bottle stopper. The pump 14 is switched on until the drip chamber 13 of the bottle 16 is half filled and the tube is filled with saline solution completely free of bubbles.

b) The three pressure measurement indicators 6 are placed in the holders and connected to the perfusion tube 18—between the perfusion tube and one pressure measurement indicator a flow transducer 3 is inserted. The spike connection 19 of the perfusion tube 18 is inserted into the water bags 1.

c) The pressure transmission hoses 10 are connected to the pressure measurement indicators 6.

d) All two-way 4 and three-way valves 5 are closed and the pressure cuff 2 is pumped up to pressurise the water bags 1.

e) To vent the pressure transmission tubes the two-way 4 and three-way valves 5 of the pressure transducer are set to "open" and are filled, without bubbles, to the top with water and the two-way valve 2 is closed again. This procedure must be carried out individually for all three pressure transmission lines.

f) The three-way valves 9 are now individually turned into the 90° position in order to electronically adjust the pressure channel to atmospheric pressure by pressing a button. The three-way valves 5 are then turned to the "open" position again.

g) The two catheters 11, 12 are placed in the urethra and rectum of the patient and connected to the pressure transmission lines and the pump tube 10.

h) The three-way valves 5 must now be individually opened again individually in order to vent the two lumens of the transurethral catheter 12 up to the tip and to fill the balloon of the rectal catheter 11.

i) The measured pressures are checked and, if necessary, zeroed by software. The system is now ready for measurement.

Figure 2:
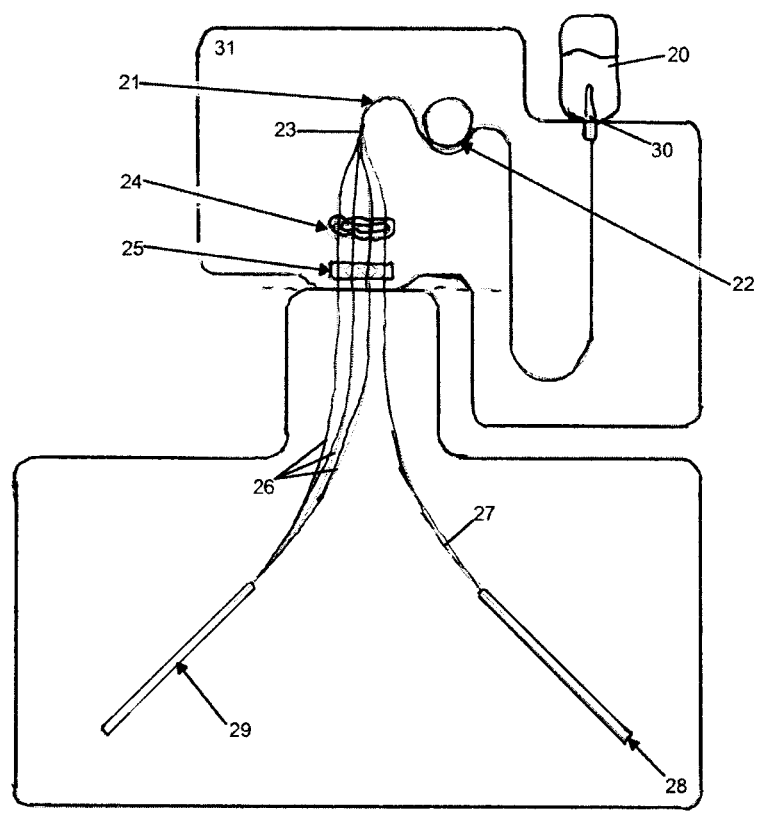
FIG. 2 shows the structure of a pressure measuring system in accordance with the present invention.

In FIG. 2 the set-up of a pressure measuring system in accordance with the invention is shown.

With reference number 21 this figure shows the pump tube leading to the pressure dome cassette 25 with the Luer locks for the connection of catheters 28 and 29. The spike connector 30 for standard infusion bottles 20 is also shown. 29 denotes the transurethral and 28 the rectal catheter (possible also any number of catheters or measuring volumes) which are supplied with the fluid via the lines 26 (three stages) and 27. Arranged adjoining this is the locking mechanism of the dome cassette 25. Arranged in the area denoted as 24 are four (possibly any number) of tube clips with the statuses "open", "closed" and "perfused". A roller pump 22 for conveying the medium through the tube system is shown. The system also has a control system 31 with a fully automated algorithm for venting the tube system with catheters, determining rest pressure and zeroing the measuring system using the functionality of the individual components.

In FIGS. 3a-3h various settings (open, closed, perfused) of the device 41 for regulating the volumetric flow, i.e. the tube clamp are shown.

In the upper row 3a to 3c a view from above of a corresponding device 41 is shown, in which the tube 42 is inserted. In the tube in the lower half, a thread 43 in the form of a spacer can be seen. In addition, the clamping element 44 and, interacting with it, the counter-wall 45 of the device 41 is shown. In FIG. 3a the open position, in FIG. 3b the completely close position and in FIG. 3c the so-called perfused, i.e. slight open, position is shown.

FIGS. 3d to 3f show cross-sectional views from FIGS. 3a to 3c along the relevant lines A-A, B-B and C-C. Here too the inserted tube 42 with the space 43 can be seen which is placed in the accommodating section 46 of the device 41. Reference number 44 denotes the clamping element which is arranged on a rotatable guide 47. The latter can interact with the wall section 45 in the various position (see 3c and 3f), wherein in accordance with the view show here, in the position according to FIGS. 3b and 3e the tube is completely close and in the position according to FIGS. 3c and 3f the tube is slightly open, although the clamping element 44 interacts with the counter-wall 45. However, in spite of squeezing of the tube, the spacer 43 brings about a slight fluid flow. In FIGS. 3g and 3h detailed views of the two positions 3e and 3h are shown in order to illustrate the difference between closed and perfused. The slight opening of the tube can be clearly seen in FIG. 3h.

Such a device 41 can also be called a tube clamp. The tube clamps replace the two-way and three-way valves used in conventional pressure measurement. They also act as a perfusion regulator for pressure measurement channels that have to be perfused (urethral pressure in urodynamic). The clamps can be brought into the positions "open", "closed" and "perfused" by simply turning about the axis with any actuator.

Position "open": in this position the filling medium can pass the tube clamp unhindered. It is the start and end position for all channels in which the tube system can be simply inserted or removed, is also used for venting the measuring channels and is the normal operating state of the infusion channel.

Position "closed": in this position the tube is completely clamped and even at pressure differences up to 2 bars it is impassable for the fluid. It is the operating state for already vented measuring channels and the temporary initial state for the infusion channel when the measuring channels are vented or perfused.

Position "perfused": in this position, largely independently of the admission pressure, only very small quantities of the filling medium (max. 8 ml/min) can pass the clamping point. This is achieved in that even though the tube is clamped with fully force in similar manner to the "closed position", in the wall of the tube a small opining is always kept free by a spacer, such a thread, which brings about a capillary reduction of the filling medium flow. This position is used for channels which require perfusion (urethral pressure).

Figure 4:
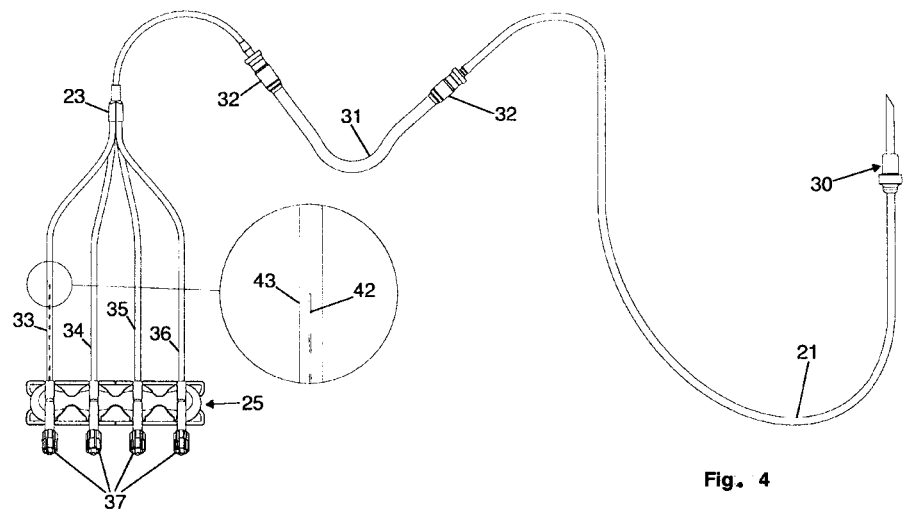
FIG. 4 shows a detailed view of the pump tube for the pressure-measuring system in accordance with the invention.

Integrated in the pump tube—as shown in FIG. 4—are the infusion tube 21, the venting hoses 34 to 36 for the three—possibly any number of—pressure channels and the dome cassette 25. The pump/infusion tube 21 also has a spiked connection 30 for an infusion bag and Luer locks 37 for connection of the catheter. When using the system with a roller pump the tube system has a suitable compressible tube segment 31 in this segment which it integrated into the tube system through appropriate connectors 32. Via the distributor 23 the tube system is dispersed over the four hoses 33 to 36 shown here. In addition to the actual tube 42, the tube 33 also comprises the spacer 43 as can be seen in the detailed view in FIG. 4.

Particularly advantageous in the present invention is the integration of three—possibly any number—of domes in a dome cassette and the common coupling of the channels to the sensors via a pressing roller and the clamping edge. Webs integrated into the dome cassette act on the pressing roller and clamping edge side as spring elements, which produce the required pressing pressure of the membranes, which are preferably arranged on the base section of the pressure domes, on the sensors.

This design has the great advantage over the conventional solution with individual domes that production is very much more cost-effective and handling is extremely simplified. Instead of placing each dome individually on its sensor as in the previous solutions, it is sufficient to insert the cassette which through the subsequent pressing of a button is turned with the pressing roller into the "closed" position via an actuator. The previously high number of required sterile components is reduced to a single disposable product.

As in many areas of application the sensor can be placed above the measuring locations in the body, as a result of the hydrostatic force of the water column negative pressures (lower than atmospheric pressure) also occur in the dome which are then not measured through pressure on the sensor surface but through tension. To produce the suction effect required for this the contacting between the membranes and sensor must be completely airtight. For this a pressing force is required.

Figure 5:
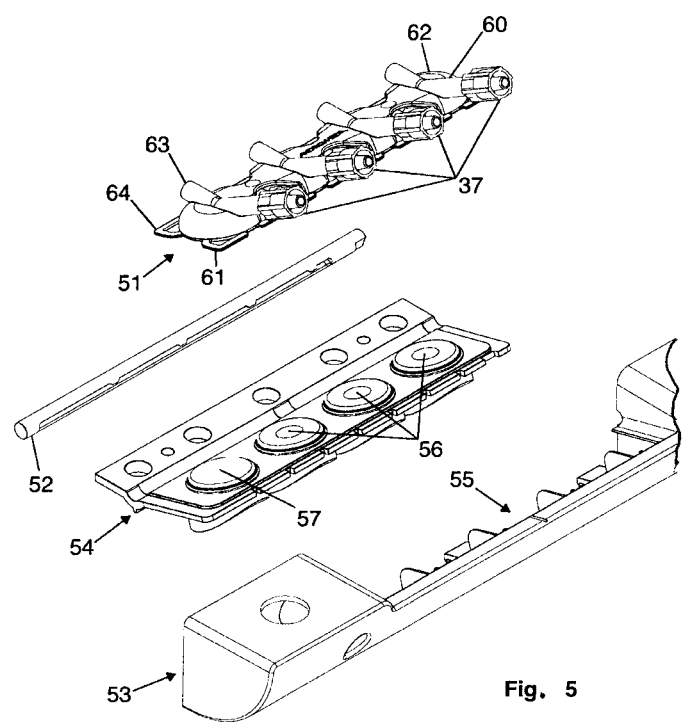
FIG. 5 shows an exploded view of the assembly of the pressure dome cassette with the pressure measuring sensors.

FIG. 5 shows an exploded view of the assembly of the pressure dome cassette 51 with the pressure measurement sensors 54. In addition to the dome cassette 51, the pressing roller 52, the holder 53 with the clamping edge 55 can be seen. Reference number 56 denotes the positions in relation to the dome cassette 51 which are fitted with a pressure measurement indicator. In position 57 no pressure measurement indicator is envisaged.

FIGS. 6a to 6d show detailed views of the dome cassette 25 and locking arrangement on the pressure measurement sensors. In FIG. 6a a side view of the dome cassette 25 is shown in which the connections 60, the pressing web 61 and parts of the fluid domes 62 can be seen. In FIG. 6b a view from above of the dome cassette 25 is shown in which the other connections 63 and the rear pressing web 64 can also be seen. FIG. 6c is a further side view in which in addition to the two connections 60 and 63 the two pressing webs 61 and 64 and the angle arrangement of the supply lines 60 and 63 with regard to each other with angle α and with regard to the base with angle β are shown.

FIG. 6d shows the arrangement of the dome cassette 25 on the pressure measurement indicators, wherein the dome cassette 25 is aligned via the pressing web 61 in the holder 53 and fixed by means of the pressing roller 52 and its axial slit in combination with turning. The holder 53 also comprises the guide 69 and 68 as a direct or indirect component part of the holder, which in the corresponding positions also comprises the pressure measurement indicator (not shown here). In addition to the holder, in this view the connections 60 and 63 can also be seen, wherein the connection 60 also has a Luer lock 65.

Figure 7:
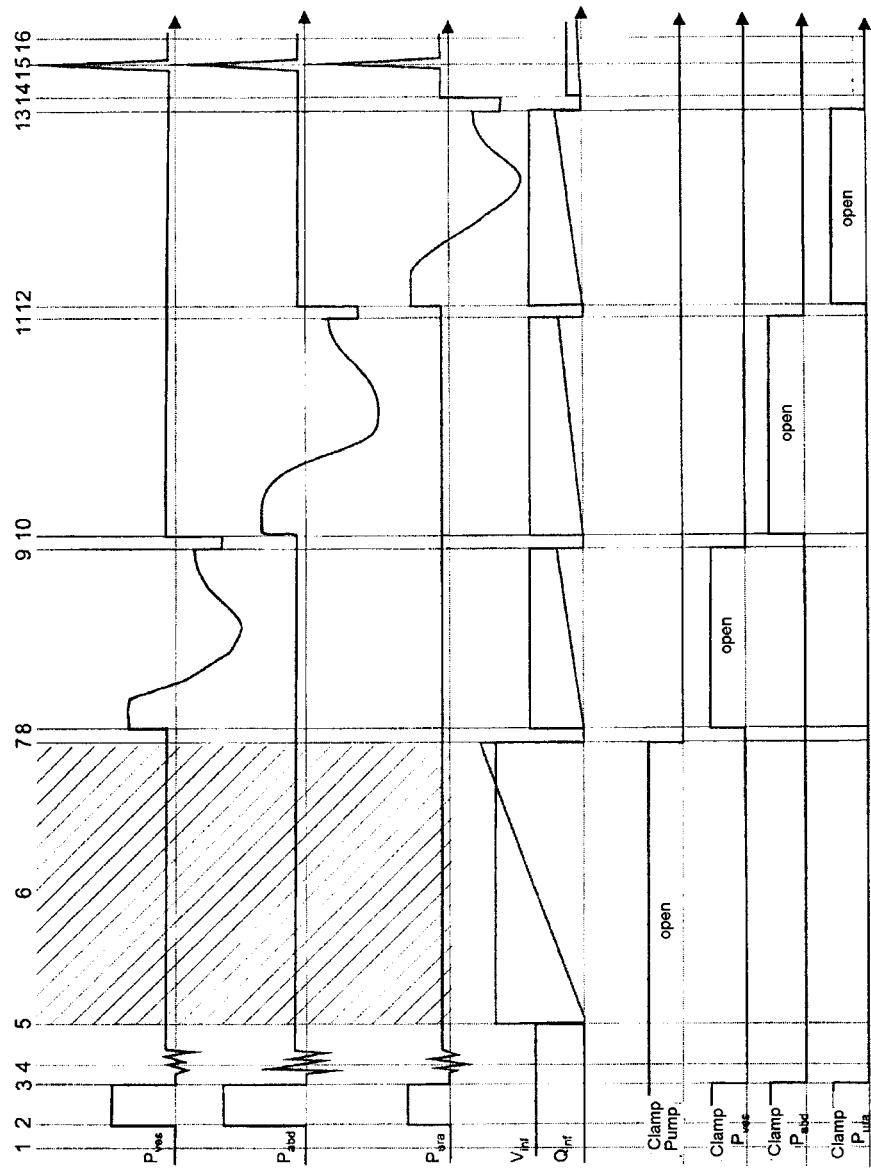
FIG. 7 shows a measuring protocol of automatic venting and zeroing of the pressure measuring system in accordance with the invention.

In FIG. 7 by way of the process stages the course of the pressure at the corresponding positions or settings of the components is shown. $P_{ura}$, $P_{ves}$, and $P_{abd}$ stand for the pressure in the corresponding pressure domes, $V_{inf}$ and $Qi_{nf}$ for the infusion volume and the fluid flow and clamp pump, clamp and clamp $P_{ves}$ for the switching position of the $P_{ura}$ clamp $P_{abd}$ corresponding tube clamp. The process is described as anebow:

1) The user places the dome cassette 25 of the pump tube 21 into the device and inserts the spike connection 30 into the infusion bag 20.

2) The locking mechanism is closed, whereby through the pressing pressure of the domes 25 on the sensors a pressure offset occurs.

3) The pressure offset is automatically balanced out (zeroed) after a material relaxation time of 5-10 seconds. At the same times the tube clamps 24 of the pressure channels 26 and 27 are closed.

4) The user places the transurethral catheter 29 in the bladder and the rectal catheter 28 in the rectum of the patient (if this has not already been done) and connects the pump tube 21 and the pressure transmission tubes with the Luer locks of the dome cassette 25. As of this moment the user can check the correct placement of the catheter 28, 29 by means of rest pressure values shown on the device, which are now measured via the air columns of the pressure transmission tubes and catheter lumen.

5) If the rest pressures show plausible values, the user starts the fully automatic venting and zeroing procedure by pressing a button on the device, whereupon the entire infusion line is vented.

6) In the hatched time interval all the measuring changes measure the rest pressure at the relevant measuring site via the air column. In order to minimise any fluctuations through movement of the patients or disturbances the average value measured by the channel during this period is calculated and subsequently use as the rest pressure value for zeroing.

7) As the volume of the infusion line (tube plus filling volume of the catheter) is precisely known and the quantity of the filling medium conveyed through the volume transducer and rotations of the rolling wheel of the pump 22 is constantly measured, the venting can be fully automatically ended when the water column reaches the filling lumen output. The pump tube clamp 24 is closed.

8, 10, 12) The venting of the pressure transmission tubes than always takes place sequentially in the same way. The relevant tube clamp is opened, while all the others are closed and the pump conveys the filling medium at a defined filling rate through the relevant pressure transmission line. It should be noted, that during filling, due to the increasing water column a hydrostatic and also a dynamic component are increasingly added and no longer is the actual pressure at the measuring location determined.

9, 11, 13) As the volumes of the pressure transmission lines are known and the filling quantity is constantly measured the venting process can be fully automatically ended when the water column has reached the measuring lumen outputs. The pump 22 is stopped and the relevant tube clamp 24 closed. At this moment the device measures the current pressure at the measuring location in the body plus a hydrostatic pressure resulting from the unknown difference in height between the measuring location and the sensor. This is now fully automatically calculated by setting the measuring channel to the rest pressure measured via the air column in (6) by means of the software.

14, 15) The correct placement of the catheter is checked in a final stage by asking the patient to cough and comparing the resulting pressures peaks. For this the tube clamps 24 of all channels which required perfusion for the measurement ($P_{ura}$ in urodynamics) are automatically set to the perfusion setting and the pump 22 to perfusion speed.

16) The preparatory phase is completed and the actual measurement can begin.

The invention claimed is:

1. A pressure-measuring system, comprising:
a tube system that defines a first measuring lumen which can be filled with a fluid and is connectable to (a) a fluid reservoir serving as a supply of the fluid and to (b) at least one catheter lumen of at least one catheter, and
a mechanism for conveying the fluid through the tube system and into the at least one catheter,
at least a first pressure measuring device and a second pressure measuring device, each said pressure measuring device including a pressure transducer membrane and a measuring chamber which can be filled with the fluid;
at least a first flow regulation device and at least one non-perfusion flow regulation device;
wherein the tube system further includes at least one coupling element which mechanically connects each said measuring chamber via its respective pressure transducer membrane with a measuring area of a pressure transducer and each said measuring chamber has at least two measuring chamber connection points for flow of the fluid therethrough;
the first flow regulation device (i) is positioned between the first pressure measuring device and the supply of the fluid, with a perfusion tube section made of a flexible material and having a perfusion tube section lumen through which the fluid can flow and (ii) has a first tube clamp into which the perfusion tube section is inserted;
the first flow regulation device can be set to open, closed and perfused regulation positions, wherein in the closed position the perfusion tube section lumen is completely squeezed closed and in the perfused position, through a spacer in the inside of the perfusion tube section, the perfusion tube section lumen is partly open even when squeezed by the first tube clamp;
wherein the first tube clamp has a first housing with a first accommodating area for the perfusion tube section and a first clamping element that can be moved between said three regulation positions, and wherein the first clamping element in interaction with sections of the first accommodating area as pressing points in at least one of said regulation positions acts on the perfusion tube section and its perfusion tube section lumen by squeezing; and
wherein the at least one non-perfusion flow regulation device has (i) a non-perfusion tube clamp having a second housing with a second accommodating area for a second, non-perfusion tube section having a non-perfusion tube section lumen and (ii) a second clamping element that can be moved between open and closed non-perfusion regulation positions, and wherein the second clamping element in interaction with sections of the second accommodating area as pressing points in at least the closed non-perfusion regulation position acts on the non-perfusion tube section lumen by squeezing.

2. The pressure-measuring system according to claim 1, wherein each said coupling element has a clamping edge and at least one rotatably borne pressing roller and each said measuring chamber has two webs arranged opposite each other, wherein one of the webs engages the clamping edge and the other web engages into the pressing roller.

3. The pressure-measuring system according to claim 2, wherein the pressing roller is capable of being moved manually or by a motor in corresponding positions.

4. The pressure-measuring system according to claim 3, wherein the first clamping element is arranged in a rotating manner about a centre of rotation and extends radially around the centre of rotation.

5. The pressure-measuring system according to claim 4, wherein the first clamping element is moved by the motor between the perfusion regulation positions and is held in each of the perfusion regulation positions.

6. The pressure-measuring system according to claim 1 wherein the lumen of the perfusion tube section has an inner diameter between 0.2 mm and 10 mm.

7. The pressure-measuring system according to claim 1 wherein at least one of (i) the spacer is an integral component of the perfusion tube section and the spacer non-uniformly reduces the lumen of the perfusion tube section and (ii) the spacer is formed by an elongated thread or rod that non-uniformly reduces the lumen of the perfusion tube section.

8. The pressure-measuring system according to claim 1 wherein cross-sectional area of the lumen is reduced by the spacer inside the perfusion tube section between 0.01% to 5%, thereby in the perfused regulation position the lumen of the perfusion tube section is kept partly open so that the fluid flows at a volumetric rate of between 0.1 ml/min and 8 ml/min.

9. The pressure-measuring system according to claim 1 wherein the measuring chamber connection points for each said measuring chamber are arranged at an angle ($\alpha$) with regard to each other of between 180° and 60°.

10. The pressure-measuring system according to claim 9, wherein the measuring chamber connection points for each said measuring chamber are arranged at an angle ($\beta$) of between 0° and 60° with regard to a base area of the measurement chamber.

11. The pressure-measuring system according to claim 1 wherein an interior of each said measuring chamber has a circular base area.

12. The pressure-measuring system according to claim 11 wherein, for each said measuring chamber, at least one, of (i) the base area is open and the pressure transducer membrane covers that base area and (ii) the pressure transducer membrane is made of a material selected from a group that contains silicone, latex, rubber, and, combinations thereof.

13. The pressure-measuring system according to claim 1 wherein the pressure transducer, membrane is centrally located in the measurement chamber to mechanically connect with the measuring area of the pressure transducer.

14. The pressure-measuring system according to claim 1 wherein an interior space of each said measuring chamber is dome-shaped.

15. The pressure-measuring system according to claim 1 wherein the fluid is selected from a group which includes water, aqueous solutions, solutions for injection, solutions for infusion, nutritional solutions, electrolyte solutions, blood, plasma, gas, air, and combinations thereof.

16. The pressure-measuring system according to claim 1 wherein at least one of the first tube clamp, said coupling elements, and said measuring chambers are at least partially made of a material selected from a group which includes duroplastic or thermoplastic synthetic materials.

17. The pressure-measuring system according to claim 1 wherein the mechanism for conveying the fluid is a peristalsis pump, a displacement pump, or a gravity pump.

18. The pressure-measuring system according to claim 1 configured for use in the field of urodynamics and gastroenterology, and wherein the at least one catheter is one of a urethral catheter, a rectal catheter, and an esophageal catheter.

* * * * *